United States Patent [19]

Kramer

[11] 4,284,502
[45] Aug. 18, 1981

[54] APPARATUS FOR TREATING UREMIC PATIENTS

[75] Inventor: Peter Kramer, Goettingen, Fed. Rep. of Germany

[73] Assignee: BASF Aktiengesellschaft, Fed. Rep. of Germany

[21] Appl. No.: 88,065

[22] Filed: Oct. 24, 1979

Related U.S. Application Data

[63] Continuation of Ser. No. 938,759, Sep. 1, 1978, abandoned.

[30] Foreign Application Priority Data

Sep. 1, 1977 [DE] Fed. Rep. of Germany ....... 2739350

[51] Int. Cl.³ .................... B01D 31/00; A61M 1/03
[52] U.S. Cl. ............................... 210/98; 128/214 F; 210/433.2
[58] Field of Search .......... 210/257 M, 321 A, 321 B, 210/416 M, 416.2 B, 98, 206; 137/564 J; 128/214 F, DIG. 3; 222/95

[56] References Cited

U.S. PATENT DOCUMENTS

| 3,199,511 | 8/1965 | Kulick | 128/214 F |
| 3,640,277 | 2/1972 | Apelberg | 128/214 F |
| 3,731,681 | 5/1973 | Blackshear et al. | 128/214 R |
| 4,041,944 | 8/1977 | Rhodes | 128/214 B |

*Primary Examiner*—Frank A. Spear, Jr.
*Attorney, Agent, or Firm*—Keil & Witherspoon

[57] ABSTRACT

An apparatus for treating uremic patients by means of ultrafiltration, in which the withdrawn blood is separated by means of a hemofilter into plasma water and residual blood and the plasma water is exchanged in an exchange device. The latter comprises two chambers I and II, separated from one another by a flexible or movable partition, of which chamber I is filled with fluid and can additionally receive the plasma water, and chamber II contains substitution solution. By exerting pressure in the partition, a suction is caused in chamber I and a pressure in chamber II, so that chamber I can take up the plasma water, while the same volume of substitution solution is released from chamber II.

5 Claims, 2 Drawing Figures

APPARATUS FOR TREATING UREMIC PATIENTS

This is a continuation of application Ser. No. 938,759 filed Sept. 1, 1978, now abandoned.

In uremic patients plasma water containing urinous substances or uremic toxins must be separated from the blood by ultrafiltration through a hemofilter after heparinization, and must, if appropriate after removal of a portion corresponding to the excretion of urine, be replaced by a substitution solution to which the dewatered residual blood is admixed before introduction into the organism.

To accelerate this process, the filtration should be assisted by a suction of the order of 40 mm Hg on the side of the plasma water, and by about an equal pressure acting on the residual blood/substitution solution mixture. Furthermore it is necessary to ensure that the patient is neither over-hydrated nor excessively dehydrated, i.e., the therapeutical amounts of liquid are adhered to precisely, and the times envisaged for these amounts are adhered to with reasonable precision. The "artificial kidneys" hitherto employed for this purpose are very expensive and, because of their complicated technology, entail safety hazards which can occur as a result of exhaustion, during treatment, of the energy sources which the kidneys require, or due to failure or wear of electromechanical control components, or due to damage to the blood cells. Furthermore, the use of blood pumps entails the risk of air embolisms.

The present invention relates to an apparatus for treating uremic patients which does not suffer from these disadvantages, and in which the freshly withdrawn blood is separated by means of a hemofilter into plasma water and residual blood and the plasma water is then passed into an exchange device, from which a substitution solution is returned into the blood circulation after combination with the residual blood, wherein the exchange device consists of a container which is completely filled with fluid and can be closed air-tight, the container comprising two chambers I and II, separated from one another by a flexible or movable partition, of which chamber I is filled with fluid and can additionally take up the plasma water and chamber II is filled with substitution solution, and wherein a suction can be caused in chamber I and a pressure in chamber II by exerting pressure on the partition.

The plasma water obtained by hemofiltration flows into chamber I and displaces from chamber II an identical volume of the substitution solution contained therein, in accordance with the volume displacement principle. This substitution solution is mixed with the residual blood which remains after passing the hemofilter and is introduced into a vein of the body.

The partition between chambers I and II is displaceable or deformable, so that a weight acting thereon produces a suction, which assists the filtration process, in chamber I, and at the same time produces a pressure, which assists the return of the substitution solution, in chamber II.

The plasma water can either be introduced into the tightly closed chamber I which is already completely filled with fluid or, advantageously, into a bag contained therein. The substitution solution in chamber II is preferably contained in a bag or in a plurality of bags connected to one another.

It is also possible to transmit the pressure from chamber II into a subsidiary chamber containing the substitution solution.

Chamber II can also comprise a bag or a plurality of bags, located in chamber I. However, in that case the pressure normally prevailing in chamber II must be transmitted directly to the bag or bags.

The amount of substitution solution supplied as a replacement for the plasma water can be reduced for therapeutic dehydration purposes. This can be achieved by branching off an appropriate amount of plasma water before the latter enters chamber I or branching off an appropriate amount of fluid from chamber II. For this purpose, it is possible to use a bag or a further chamber, located outside chambers I and II and connected via a valve to the hemofiltrate line or to the chamber II.

The novel apparatus is substantially cheaper than the conventional dialysis apparatus. Furthermore, it offers a high degree of safety (as a result of dispensing with a blood pump, the risk to the patient of an air embolism is excluded, so that the apparatus can be employed at home. Finally, the apparatus is independent of the water mains and of the electrical mains supply.

Figure 1:
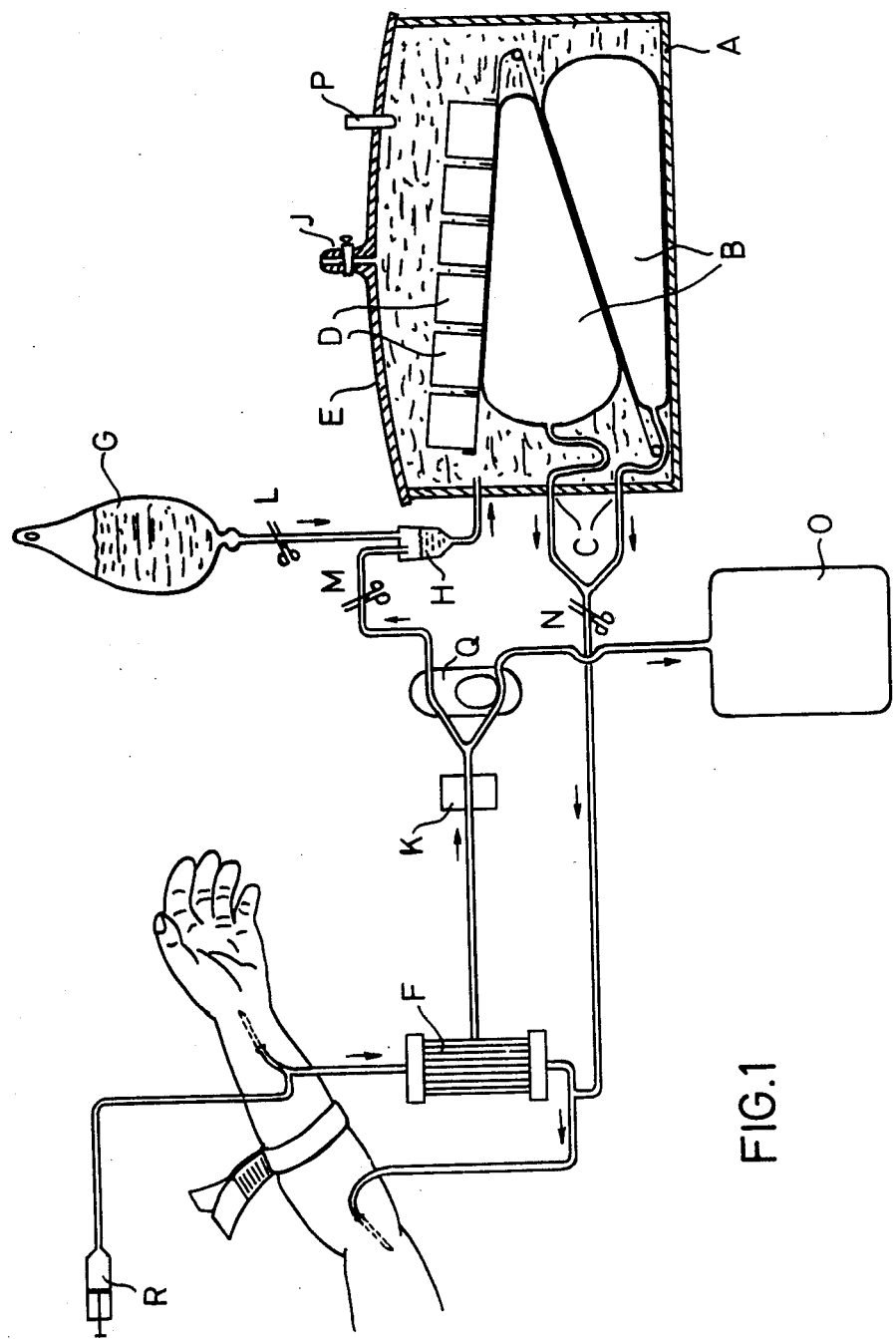
FIG. 1 depicts a view of apparatus according to this invention connected to a patient. The exchange device is shown in a sectional view.
Figure 2:
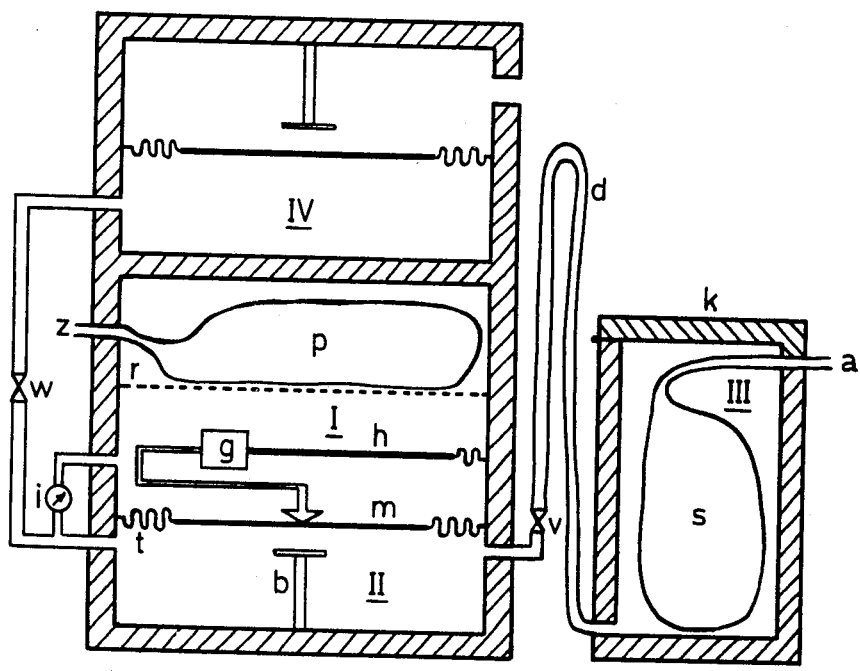
FIG. 2 is a sectional view of an alternate embodiment of the invention.

FIG. 1:

Two 5 liter bags containing substitution solution B are placed in a container A which can be closed airtight by means of a lid, and the connecting nozzles of the bags are led out of the container through special seals C in one of the side walls. The connecting tubes joined to the tube through which the residual blood passes, downstream from the hemofilter, are filled with solution and then closed by means of a clip N. The pressure of the weights (from 20 to 40 kg) is transmitted to the infusion bags. This for example produces a pressure of from 40 to 80 mm Hg in the infusion bags. The container is filled to the rim with water free from air bubbles, and is closed with the lid E. Residual air which has collected in the dome of the lid is expelled through the venting valve N by opening the additional infusion bag G which enters the container via the drip chamber and the ultrafiltration inlet H, and the venting valve is then closed.

The amount of substitution solution forced out of this closed container by the pressure of the weights is now only equal to the amount of ultrafiltrate which flows into the container. The weights not only produce a pressure in the infusion bags but also a suction in the fluid surrounding the infusion bags. This suction assists the entry of ultrafiltrate or plasma water after the apparatus has been connected to the patient. The blood is forced through the hemofilter by utilizing the arteriovenous pressure gradient (ie. by cardiac pressure), with the suction caused by the weights D assisting the filtration. Blood losses through a rupture in the membrane should trigger an early alarm by means of a turbidimeter K which scans the tube through which the ultrafiltrate passes. The rate of ultrafiltration can be estimated from the drip rate in the drip chamber H.

When, at the start of the treatment, the additional infusion line (clip L) is closed and the tubes through which the ultrafiltrate and the substitution solution pass (clips M and N) have been opened, the amount of the ultrafiltered plasma water is replaced quantitatively by substitution solution. Effective withdrawal of fluid is achieved by branching off a part of the ultrafiltrate into the air-free collecting bag O. A slight suction is produced hydrostatically by suspending the collecting bag below the patient. The ultrafiltration stream is then released by an alternating pinch valve Q, with an infinitely variable electronic interval switch, either in the direction of the substitution container A or of the collecting bag O. Quasi-continuous withdrawal of fluid can be achieved by suitable choice of the time intervals (for example 48 sec→substitution container/12 sec→collecting bag). With a filtration rate of 10 ml/min, the patient then loses 2 ml/min or 120 ml/h. Excessive abstraction of fluid is prevented by the limited capacity of the collecting bag O (from 1.5 to 2.5 liters). Excessive supply of fluid, resulting from air penetrating into the container A, is prevented by a fluid level monitoring device P (luminous glass reflection probe). When the glass cone of this probe loses contact with the fluid, an alarm is triggered.

Heparin can be added to the blood fluid by means of the heparin pump R. This heparin pump, like the turbidimeter K, the pinch valve Q and the fluid level monitoring device P, can be operated by means of batteries.

FIG. 2:

Two closed chambers I and II of transparent rigid material are connected by a leaktight flexible partition t to a rigid middle portion m, on which presses a rotatable lever h, which carries a weight g which can be caused to slide on said lever by external means. In chamber I, above the weight device, there is a grid r on which rests a plasma water collecting bag p, whose inlet tube z leads out through the wall of the chamber via a gland in which the tube is embedded. Chamber II contains a stop b by means of which the maximum deflection of partition t can be limited by external means. in addition, a pressure tube d leads from chamber II to a subsidiary chamber III, the height of which is adjustable and which possesses a flap lid k by means of which it can be closed tightly. A filled substitution solution bag s is suspended in this subsidiary chamber, the connecting tube a leading out from the chamber, through a gland, without being pinched. Chambers I and II are filled with a hydraulic fluid, for example, water.

To prepare for the treatment, a filled bag S containing substitution solution is first introduced into the chamber III and the latter is closed tightly. Chambers I, II and III are then vented (by means of valves and connections not shown in the drawing) with the required fluid running in from an upper chamber IV and emptying plasma water bag p whilst valve v and outlet a of the apparatus are still closed. At this point in time, chamber III is at about the same height as chamber II, for example they may be standing on one and the same table top. The connections to chamber IV, required for filling up, are then closed and the valve is opened.

The weight g exerts pressure on the fluid in chamber II via partition t, whilst there is corresponding suction in chamber I. This pressure difference can be read off directly on a differential manometer i. It can be brought to the therapeutically desired value by sliding weight g on lever h (by means of a spindle which is not shown in the drawing).

When the patient has also been connected to the hemofilter and the heparin pump, the plasma water outlet of the filter can be connected to the supply tube z and the arm of the filter through which the residual blood passes can be connected to the outlet tube a, both connections being made in such a way as not to introduce air. After opening valve v, the pressure can now be transmitted from chamber II into chamber III and can expel from the bag s in chamber III exactly as much substitution solution as the amount of plasma water which is drawn from the hemofilter into plasma collecting bag p by the suction in chamber I. This quantitative replacement of plasma water by substitution solution is terminated, by volume control, when either the substitution solution has been consumed or stop b in chamber II limits the movement of partition t. The duration of the exchange process can be varied by sliding the weight g.

To dehydrate the patient, the entire plasma water is again drawn into plasma collecting bag p, but a preselected portion of the fluid which is thereby displaced from chamber II is led via a regulating valve w into a dehydrating chamber IV. This chamber is sealed from the atmosphere by a similar dividing surface to that which separates chambers I and II. A stop, as in chamber II, makes it possible to limit the movement of the partition (and hence the volume increase in chamber IV) to the therapeutically desired dehydration volume. The desired dehydration speed is set by means of the regulating valve w.

After completion of the treatment, the connections to the filter are removed, subsidiary chamber III is raised relative to its position during the treatment, and the lid of the chamber is opened until, as a result of fluid flowing out of chamber III into chamber II, partition t, together with the weight g pressing thereon, has been forced back into its starting position, the plasma collecting bag p being emptied at the same time. Valve v between chambers II and III is then closed, chamber III is again lowered to its starting position and the empty substitution solution bag s is removed. The apparatus is then ready for the next treatment.

I claim:

1. Apparatus comprising means for treating the blood of uremic patients constructed and arranged to separate freshly withdrawn blood by means of a filter into plasma water and residual blood, the plasma water being passed into an exchange device from which a substitution solution is returned into the blood circulation after combination with the residual blood, said exchange device comprising a closed container which is completely filled with fluid and can be closed air-tight, said container further comprising separate enclosed chamber I and enclosed chamber II, which are separated from one another by a movable or flexible partition, chamber I being filled with fluid and being constructed and arranged to take up additional plasma water, and chamber II being filled with substitution solution, said exchange device further comprising means to exert pressure by weight on said partition so as to create a suction in chamber I and a corresponding pressure in chamber II.

2. The apparatus of claim 1, wherein said chamber II comprises one or more bags connected to one another onto which the pressure exerted on said partition is directly transmitted.

3. The apparatus of claim 1, wherein chamber II is enclosed in part by said partition and varies in volume depending upon the location within the container of the partition.

4. The apparatus of claim 3, further comprising enclosed subsidiary chamber III, located outside said container, which contains substitution solution in a bag therein, and which is so connected to chamber II that substitution solution running from chamber II to chamber III during treatment of a patient is able to run back from chamber III to chamber II when chamber III is raised to an elevation above that of the exchange device upon completion of a treatment of a patient with the apparatus, the substitution solution in said bag being unable to mingle with the solution around it in chamber III.

5. The apparatus of claim 4, further comprising enclosed dehydrating chamber IV separate from said container, which is connected to chamber II and which contains means for limiting its volumetric expansion to a predetermined dehydration volume, such that chamber IV takes up a preselected volume of plasma water from chamber II.

* * * * *

UNITED STATES PATENT AND TRADEMARK OFFICE
CERTIFICATE OF CORRECTION

PATENT NO. : 4,284,502
DATED : August 18, 1981
INVENTOR(S) : Peter Kramer

It is certified that error appears in the above—identified patent and that said Letters Patent is hereby corrected as shown below:

IN THE ABSTRACT

Line 10, "in the partition" should read --on the partition--.

Signed and Sealed this

Fifteenth Day of December 1981

[SEAL]

Attest:

GERALD J. MOSSINGHOFF

Attesting Officer     Commissioner of Patents and Trademarks

UNITED STATES PATENT AND TRADEMARK OFFICE
CERTIFICATE OF CORRECTION

PATENT NO. : 4,284,502
DATED : August 18, 1981
INVENTOR(S) : Peter Kramer

It is certified that error appears in the above—identified patent and that said Letters Patent is hereby corrected as shown below:

On the cover page, the Assignee should be

-- SCHI-WA Arzneimittelwerk GmbH, Fed. Rep. of Germany --

Signed and Sealed this

Thirteenth Day of April 1982

[SEAL]

Attest:

GERALD J. MOSSINGHOFF

*Attesting Officer*   *Commissioner of Patents and Trademarks*